United States Patent [19]

Suzuki

[11] Patent Number: 4,579,852

[45] Date of Patent: Apr. 1, 1986

[54] AGENT FOR AVOIDING OCCLUSION OF SHUNTS IN SUBSTITUTE BLOOD TUBES

[75] Inventor: Tadao Suzuki, Tokyo, Japan

[73] Assignee: Sopharma S.A., Geneva, Switzerland

[21] Appl. No.: 398,619

[22] Filed: Jul. 15, 1982

Related U.S. Application Data

[63] Continuation of Ser. No. 972,818, Dec. 26, 1978, abandoned.

[30] Foreign Application Priority Data

Feb. 6, 1978 [JP]  Japan ................................ 53-12180

[51] Int. Cl.$^4$ ............................................. A61K 31/44
[52] U.S. Cl. ................................................... 514/301
[58] Field of Search ........................ 424/256; 514/301

[56] References Cited

U.S. PATENT DOCUMENTS 4,051,141 9/1977 Castaigne ........................... 424/256

Primary Examiner—Jerome D. Goldberg
Attorney, Agent, or Firm—Weiser & Stapler

[57] ABSTRACT

The present invention relates to an agent for avoiding occlusion by thrombus of shunts and substitute blood tubes used in blood dialysis consisting of a compound selected from 5-(2-chlorobenzyl)-4,5,6, 7-tetrahydrothieno [3,2-c]pyridine and its therapeutically acceptable acid addition salts.

The therapeutically acceptable acid addition salt is, in particular, the hydrochloride, named Ticlopidine.

2 Claims, No Drawings

AGENT FOR AVOIDING OCCLUSION OF SHUNTS IN SUBSTITUTE BLOOD TUBES

This is a continuation of application Ser. No. 972,818, filed Dec. 26, 1978, now abandoned.

The present invention relates to a novel agent for avoiding occlusion of shunts and substitute blood tubes comprising 5-(2-chlorobenzyl)-4,5,6,7-tetrahydrothieno[3,2-c]pyridine and/or a therapeutically acceptable salt thereof.

5-(2-chlorobenzyl)-4,5,6,7-tetrahydrothieno[3,2-c]pyridine is represented by the formula:

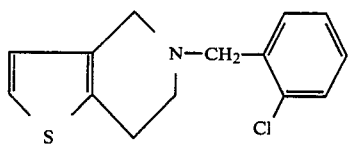

(I)

and the hydrochloride salt thereof is called Ticlopidine.

Ticlopidine and its process of preparation have been disclosed in U.S. Pat. No. 4,051,141.

Although the present invention will be explained hereinafter with reference to Ticlopidine, similar results are obtained with other acid addition salts of (I) or with the free base (I) itself.

For blood dialysis with an artificial kidney, it is necessary to prepare an external shunt connected outside the body by inserting a tube for the shunt into an artery and a vein of the forearm or a lower extremity, and either a graft for laying a substitute blood tube under the skin as a shunt for the artery and vein, or an internal shunt which directly connects the artery with the vein, in order to guide the body blood into the artificial kidney. These substitute blood tubes often tend to be occluded due to thrombus since substitute blood tubes are used for external shunts or grafts and as a result, the blood stream is often blocked. Further, internal shunts are associated with some injury of the blood endothelium due to the frequent insertion of an injection needle for collecting blood samples which causes thrombus or stenosis of the blood tube, so that there is a potential danger of a decrease in blood stream. Hereafter, an external shunt, a graft and an internal shunt will be referred to generically as shunts. When shunts are occluded, a removal of the thrombus is performed or new shunts are prepared and set. However, when the places where the shunts can be set are limited, forearm and lower extremity, it is of an extreme importance to avoid occlusion of the shunts in order to continue the blood dialysis therapy using an artificial kidney over a long period of time. For the prophylaxis or treatment of thrombus in shunts, it has been rarely attempted to use the continuous drop of urokinase, which is a thrombolytic agent, or heparin, as anticoagulant, but in such cases no satisfactorily therapeutic results have been obtained. As a result of extensive investigations on thrombus prophylactic and improving agents in shunts, the present inventor has found that Ticlopidine which is efficient in preventing platelet from coagulation meets this purpose.

According to the present invention, not only the effect of inhibiting the formation of thrombus in shunts but also the effect of recovering blood stream of patients who can not provide a sufficient amount of blood stream necessary for dialysis due to narrowing intracavity of shunts, are recognized. Clinical test results are summarized in Tables I and II.

Although the mechanism of activity of Ticlopidine is unclear, it is assumed that since Ticlopidine has the effect of peventing platelets from coagulation, the drug first inhibits coagulation of platelets, which is a primary reaction for formation of thrombus, thereby preventing the formation of thrombus. However, the mechanism of Ticlopidine is not sufficiently explainable only by the effect as anti-coagulant on platelets. In fact, in the clinical tests as shown in Table I, Aspirin or Dipyridamol, both of which are well known as anti-coagulant of platelets, had been given in the pretreatment prior to the treatment with Ticlopidine, but such pretreatments themselves were ineffective. The prevention effect from the formation of thrombus should be assumed to be due to the results brought by a medicine acting on any one of the blood coagulation mechanism, the platelet coagulation mechanism and the fibrinolysis mechanism, or combinations thereof. Assuming that Ticlopidine acts on coagulation mechanism, and if it is specifically stated, a variety of mechanisms are expected with Ticlopidine; the prevention effect from the formation of thrombus in external shunts is, for example, due to inactivation of Factor XII for blood coagulation, due to inhibition of other stages of coagulation, e.g. inhibition of thrombus formation, due to the effect of inhibitory factors of the coagulation factors, etc., or due to combined actions thereof; or the prevention effect from the formation of thrombus in external shunts is also due to inactivation of Factor VII for blood coagulation, etc. When considering such a complicated mechanism of thrombus formation, it is conceivable that, even if these two medicaments have similar prevention effect from platelet coagulation, it is merely a result of a superficial observation, but there may be a possibility that the two medicaments exhibit the prevention effect from the formation of thrombus by quite a different reason. In this sense, it is highly probable that Ticlopidine would have a prevention effect from platelet coagulation or prevention effect from blood coagulation, which quite differs from those of Aspirin or Dipyridamol. Therefore, it is believed that prevention from thrombus in shunts can be achieved, which could not be achieved with Aspirin or the like. On the other hand, it is unlikely that prevention effect from the platelet coagulation could be extended to the recovery of blood stream in narrowed shunts. Considering also this viewpoint, it is quite unknown on what mechanism the prophylactic and improving effect of Ticlopidine against thrombus formation in shunts is based. An activity other than prevention effect from the platelet coagulation is also possible.

The present invention will be explained hereinafter with reference to the clinical data shown in Tables I and II.

Table I indicates the results obtained by oral administration of Ticlopidine to 43 patients, who suffered from chronic renal dysfunction under blood dialysis therapy and were troubled with frequent formation of thrombus in their shunts, at the daily dose of 100 to 300 mg (1-3 capsules containing each 100 mg) over 2 months. To assess the effect, the frequency of thrombus formation before the Ticlopidine medication period for 2 months and during 2 months following the medication period, and the amount of blood stream during the dialysis were compared and classified into the following four stages:

Markedly effective: Obvious decrease of the number of times when thrombus was formed.

Effective: Recovered blood stream while the frequency of the thrombus formation is unchanged.

Ineffective: Unchanged both in the frequency of the thrombus formation and in blood stream.

Aggravated: Increase in the number of times of thrombus formation and/or decrease in blood stream.

Summarizing the prophylactic and improving effect of Ticlopidine against thrombus formation in shunts shown in Table I, markedly effective were 32/43 (74.4%), effective 2/43 (4.7%), ineffective 8/43 (18.6%) and aggravated 1/43 (2.3%).

Table II indicates the results obtained by measuring a mean value of the amount of blood stream before the Ticlopidine medication period, 1 month after and 2 months after during the medication period, with respect to 30 patients who showed a lowering in the amount of blood stream upon dialysis. From the results shown in Table II, it is seen that Ticlopidine has an effect of recovery of the amount of blood stream during dialysis, i.e., blood stream in shunts.

From these results, it can be seen that Ticlopidine exhibits an excellent prophylactic and improving effect against thrombus formation in shunts. On the other hand, when examining Ticlopidine from the viewpoint of its side effects, vomiting was observed with only one out of 43 patients and Ticlopidine is deemed to be medicated safely for clinical purpose.

The thrombus formation of patients under blood dialysis therapy in their shunts was examined as clinical examples and it is clear that Ticlopidine would exhibit a prophylactic and improving effect against thrombus undesirably formed in substitute blood tubes which are employed in hematogenic reconstruction.

It is believed that a suitable dose of Ticlopidine be between 100 mg and 300 mg as a daily dose in general, but it can be suitably varied depending upon symptoms. Although capsules were used in the clinical examples, the present invention is not limited thereto and tablets, powders, injections, etc. are acceptable, the active ingredient being combined with the usual pharmaceutical carriers or vehicles.

TABLE I

| No. | Name | Sex | Age | Primary Disease | Kind of Shunt | Dose mg/day | Effect Assessment | | | Side Effect | Medicament in Pretreatment |
|---|---|---|---|---|---|---|---|---|---|---|---|
| | | | | | | | Thrombus in Shunt | Blood Stream | Total Assessment | | |
| 1 | TI | ♀ | 60 | diabetes | external shunt | 100 | decreased | | markedly effective | | |
| 2 | TI | ♀ | 36 | chronic nephritis | " | 200 | " | | markedly effective | | |
| 3 | YO | ♀ | 23 | nephropathia of pregnancy | " | 200 | " | | markedly effective | | |
| 4 | TH | ♂ | 35 | chronic nephritis | graft | 200 | " | recovered | markedly effective | | |
| 5 | NY | ♂ | 22 | purpura | " | 100 | " | " | markedly effective | | |
| 6 | AM | ♀ | 43 | chronic nephritis | " | 200 | " | " | markedly effective | | |
| 7 | TI | ♂ | 43 | chronic nephritis | " | 100 | " | " | markedly effective | | |
| 8 | TH | ♂ | 55 | chronic nephritis | external shunt | 200 | " | unchanged | markedly effective | | Aspirin 1 g/day |
| 9 | TY | ♂ | 33 | chronic nephritis | " | 100 | unchange | " | ineffective | | |
| 10 | TN | ♀ | 54 | chronic nephritis | " | 200 | decreased | recovered | markedly effective | | |
| 11 | SS | ♀ | 57 | chronic nephritis | " | 200 | unchanged | unchanged | ineffective | | |
| 12 | SO | ♀ | 40 | chronic nephritis | " | 300 | decreased | recovered | markedly effective | | |
| 13 | SS | ♀ | 38 | | " | 300 | " | " | markedly effective | | |
| 14 | MM | ♀ | 59 | chronic nephritis | graft | 300 | " | | markedly effective | | |
| 15 | AM | ♀ | 30 | chronic nephritis | external shunt | 300 | " | " | markedly effective | | Dipyri damol 375 mg/day |
| 16 | MI | ♂ | 62 | chronic nephritis | " | 300 | " | improved | markedly effective | | Aspirin 0.6 g/day |
| 17 | SE | ♀ | 41 | chronic nephritis | " | 300 | unchanged | unchanged | ineffective | | |
| 18 | FT | ♀ | 49 | chronic nephritis | " | 300 | decreased | recovered | markedly effective | | |
| 19 | FM | ♀ | 56 | chronic nephritis | " | 300 | unchanged | " | effective | | |
| 20 | HI | ♂ | 65 | chronic nephritis | " | 200 | " | lowered | aggravated | | |
| 21 | SF | ♂ | 56 | chronic nephritis | " | 100 | decreased | recovered | markedly effective | | |
| 22 | MH | ♀ | 54 | chronic nephritis | " | 100 | " | unchanged | markedly effective | | |
| 23 | SN | ♂ | 60 | chronic nephritis | " | 200 | unchanged | " | ineffective | | |
| 24 | KN | ♂ | 55 | chronic nephritis | " | 200 | decreased | recovered | markedly effective | | |
| 25 | KM | ♂ | 47 | chronic nephritis | graft | 200 | " | | markedly effective | | |
| 26 | KS | ♀ | 50 | chronic | " | 200 | " | | markedly | | |

TABLE I-continued

| No. | Name | Sex | Age | Primary Disease | Kind of Shunt | Dose mg/day | Thrombus in Shunt | Blood Stream | Total Assessment | Side Effect | Medicament in Pretreatment |
|---|---|---|---|---|---|---|---|---|---|---|---|
| 27 | SN | ♀ | 39 | nephritis chronic nephritis | " | | unchanged | | effective ineffective | | |
| 28 | KK | ♀ | 45 | chronic nephritis | " | 200 | decreased | | markedly effective | | |
| 29 | HI | ♀ | 43 | chronic nephritis | " | 200 | unchanged | | ineffective | | |
| 30 | EW | ♂ | 54 | chronic nephritis | " | 200 | decreased | | markedly effective | | |
| 31 | SM | ♂ | 64 | chronic nephritis | external shunt | 300 | " | | markedly effective | | urokinase 12,000 unit/day |
| 32 | RN | ♂ | 56 | chronic nephritis | " | 200 | " | " | markedly effective | | urokinase 12,000 unit/day heparin 1000 unit/time |
| 33 | EY | ♀ | 50 | chronic nephritis | " | 200 | unchanged | unchanged | ineffective | | |
| 34 | MU | ♀ | 39 | chronic nephritis | " | 200 | decreased | | markedly effective | | |
| 35 | HF | ♀ | 45 | SLE | " | 200 | " | | markedly effective | | |
| 36 | KO | ♂ | 55 | chronic nephritis | " | 200 | " | | markedly effective | | |
| 37 | SK | ♀ | 65 | chronic nephritis | " | 100 | " | | markedly effective | | |
| 38 | SI | ♂ | 37 | chronic nephritis | " | 300 | " | | markedly effective | vomiting | |
| 39 | MA | ♂ | 50 | chronic nephritis | " | 300 | " | | markedly effective | | |
| 40 | TN | ♀ | 52 | chronic nephritis | " | 300 | " | | markedly effective | | |
| 41 | MH | ♀ | 62 | chronic nephritis | " | 200 | " | recovered | markedly effective | | Aspirin 1 g/day |
| 42 | KI | ♂ | 29 | | internal shunt | 300 | | unchanged | ineffective | | |
| 43 | TY | ♂ | 57 | diabetes | " | 100 | | recovered | effective | | |

TABLE II

| Blood Stream Amount during Dialysis (ml/min) | | |
|---|---|---|
| before Ticlopidine medication | 1 month after Ticlopidine medication | 2 months after Ticlopidine medication |
| 147.3 ± 6.6 | 165.7 ± 6.2* | 176.2 ± 5.8* |

Numerical values indicate mean values ± standard error.
*significant difference $p < 0.05$ (Level of significance)

Having now described my invention what I claim as new and desire to secure by Letters Patent is:

1. A method for controlling blood thrombus in shunts of a patient suffering from chronic renal dysfunction, which patient is under blood dialysis therapy assisted by an artificial kidney apparatus which is connected with associated extracorporeal shunts to guide the patient's blood into the artificial kidney and return the blood to the patient, which comprises the steps of orally administering to the patient in conjunction with said blood dialysis therapy, a compound selected from the group consisting of 5-(2-chlorobenzyl)-4,5,6,7-tetrahydrothieno[3,2-c]pyridine and its therapeutically acceptable acid addition salts in an amount effective for decreasing the occurence of thrombus in the blood in said shunts, causing blood flow from said patient and through said extracorporeal shunts and artificial kidney decreasing the occurrence of thrombus by the action of said compound in said shunt, and returning said treated blood to said patient, and repeating the recirculation of said blood from said patient through said shunts and artificial kidney.

2. The method of claim 1 wheren the compound is administered in a daily dose of 100 mg. to 300 mg.

* * * * *